(12) United States Patent
Hoffman et al.

(10) Patent No.: US 8,551,517 B2
(45) Date of Patent: Oct. 8, 2013

(54) SUBSTRATES PROVIDING MULTIPLE RELEASES OF ACTIVE AGENTS

(75) Inventors: Douglas Robert Hoffman, Greenville, WI (US); Andrea Jo Smiltneek, Appleton, WI (US); Sara Ann Carney, De Pere, WI (US); Scott W. Wenzel, Neenah, WI (US); David William Koenig, Menasha, WI (US); Jeffery Richard Seidling, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 612 days.

(21) Appl. No.: 12/336,243

(22) Filed: Dec. 16, 2008

(65) Prior Publication Data

US 2010/0150989 A1 Jun. 17, 2010

(51) Int. Cl.
| A61K 9/70 | (2006.01) |
| A61L 31/12 | (2006.01) |
| A61L 2/232 | (2006.01) |
| A01N 25/34 | (2006.01) |

(52) U.S. Cl.
USPC ............ 424/443; 424/405; 424/447; 424/486

(58) Field of Classification Search
None
See application file for complete search history.

(56) References Cited

U.S. PATENT DOCUMENTS

| 3,966,902 | A | 6/1976 | Chromecek |
| 4,500,337 | A | 2/1985 | Young et al. |
| 4,643,181 | A | 2/1987 | Brown |
| 4,655,756 | A | 4/1987 | Fawkes |
| 4,828,912 | A | 5/1989 | Hossain et al. |
| 4,837,079 | A | 6/1989 | Quantrille et al. |
| 4,853,978 | A | 8/1989 | Stockum |
| 4,897,304 | A | 1/1990 | Hossain et al. |
| 4,948,592 | A | 8/1990 | Ayer et al. |
| 5,069,907 | A | 12/1991 | Mixon et al. |
| 5,141,803 | A | 8/1992 | Pregozen |
| 5,180,585 | A | 1/1993 | Jacobson et al. |
| 5,213,808 | A | 5/1993 | Bar Shalom et al. |
| 5,300,167 | A | 4/1994 | Nohr et al. |
| 5,310,559 | A | 5/1994 | Shah et al. |
| 5,567,372 | A | 10/1996 | Nohr et al. |
| 5,717,030 | A | 2/1998 | Dunn et al. |
| 5,804,538 | A * | 9/1998 | Wei et al. ...................... 510/101 |
| 5,817,325 | A | 10/1998 | Sawan et al. |
| 5,869,073 | A | 2/1999 | Sawan et al. |
| 5,906,825 | A | 5/1999 | Seabrook, Jr. et al. |
| 6,096,070 | A | 8/2000 | Ragheb et al. |
| 6,153,208 | A | 11/2000 | McAtee et al. |
| 6,168,800 | B1 | 1/2001 | Dobos et al. |
| 6,180,584 | B1 | 1/2001 | Sawan et al. |
| 6,197,322 | B1 | 3/2001 | Dutkiewicz et al. |
| 6,530,951 | B1 | 3/2003 | Bates et al. |
| 6,586,000 | B2 | 7/2003 | Luo et al. |
| 6,592,885 | B2 | 7/2003 | Phaneuf et al. |
| 6,712,121 | B2 | 3/2004 | Clark et al. |
| 6,730,064 | B2 | 5/2004 | Ragheb et al. |
| 6,767,508 | B1 | 7/2004 | Yahiaoui et al. |
| 6,774,278 | B1 | 8/2004 | Ragheb et al. |
| 6,793,936 | B2 | 9/2004 | Devane et al. |
| 6,824,561 | B2 | 11/2004 | Soykan et al. |
| 6,835,865 | B2 | 12/2004 | Quincy, III |
| 6,887,270 | B2 | 5/2005 | Miller et al. |
| 6,916,480 | B2 | 7/2005 | Anderson et al. |
| 6,918,927 | B2 | 7/2005 | Bates et al. |
| 6,939,569 | B1 | 9/2005 | Green et al. |
| 6,989,156 | B2 | 1/2006 | Gillis |
| 7,220,491 | B2 | 5/2007 | Rouns et al. |
| 7,264,859 | B2 | 9/2007 | Rouns et al. |
| 7,354,605 | B2 | 4/2008 | Trogolo et al. |
| 2002/0006886 | A1 | 1/2002 | Beerse et al. |
| 2003/0054185 | A1 | 3/2003 | Ottersbach et al. |
| 2003/0118658 | A1 | 6/2003 | Trogolo et al. |
| 2004/0013638 | A1 | 1/2004 | Aubay et al. |
| 2004/0048768 | A1 | 3/2004 | Clark et al. |

(Continued)

FOREIGN PATENT DOCUMENTS

| EP | 0 136 900 A2 | 4/1985 |
| GB | 2 397 523 A | 7/2004 |

(Continued)

OTHER PUBLICATIONS

Gravesen, Anne et al., "Surface Attachment of *Listeria monocytogenes* is Induced by Sublethal Concentrations of Alcohol at Low Temperatures," *Applied and Environmental Microbiology*, vol. 71, No. 9, Sep. 2005, pp. 5601-5603.

(Continued)

*Primary Examiner* — Robert A Wax
*Assistant Examiner* — H. Sarah Park
(74) *Attorney, Agent, or Firm* — Denise L. Stoker; R. Joseph Foster, III

(57) ABSTRACT

The present disclosure comprises a polymeric substrate that provides multiple releases of active agents. A substrate for multiple phase delivery of active agents is provided having a first polymer matrix layer having a first active agent disposed therein, a second polymer matrix layer having a second active agent disposed therein, and a coacervate layer disposed between the first polymer matrix layer and the second polymer matrix layer. Selected first and second active agents are included in the first and second polymer matrices such that as the first and second polymer matrices dissolve, the active agents are released. Multiple phase active agent release is achieved by constructing multiple layers of a polymer matrix containing an active agents formed with polymers having different solubility characteristics or with active agents at different concentration levels.

16 Claims, 2 Drawing Sheets

(56) References Cited

U.S. PATENT DOCUMENTS

| | | | |
|---|---|---|---|
| 2004/0082925 | A1 | 4/2004 | Patel |
| 2004/0087226 | A1 | 5/2004 | Watanabe et al. |
| 2004/0147189 | A1 | 7/2004 | Smith et al. |
| 2004/0151919 | A1 | 8/2004 | Bagwell et al. |
| 2004/0259445 | A1 | 12/2004 | Hilfenhaus et al. |
| 2005/0033251 | A1 | 2/2005 | Toreki et al. |
| 2006/0147502 | A1 | 7/2006 | Koenig et al. |
| 2006/0210600 | A1 | 9/2006 | Nolting |
| 2007/0044801 | A1 | 3/2007 | Mathis et al. |
| 2007/0048358 | A1* | 3/2007 | Schorr et al. .............. 424/443 |
| 2007/0298067 | A1* | 12/2007 | Kangas ..................... 424/423 |

FOREIGN PATENT DOCUMENTS

| | | |
|---|---|---|
| JP | 2002-065879 A | 3/2002 |
| WO | WO 2004/037115 A2 | 5/2004 |
| WO | WO 2004/087226 A1 | 10/2004 |

OTHER PUBLICATIONS

Knobloch, Johannes K.-M. et al., "Alcoholic Ingredients in Skin Disinfectants Increase Biofilm Expression of *Staphylococcus epidermidis,*" *Journal of Antimicrobial Chemotherapy*, vol. 49, No. 4, Apr. 2002, pp. 683-687.

Knobloch, Johannes K.-M. et al., "Biofilm Formation by *Staphylococcus epidermidis* Depends on Functional RsbU, an Activator of the sigB Operon: Differential Activation Mechanisms Due to Ethanol and Salt Stress," *Journal of Bacteriology*, vol. 183, No. 8, Apr. 2001, pp. 2624-2633.

Rachid, Shwan et al., "Effect of Subinhibitory Antibiotic Concentrations on Polysaccharide Intercellular Adhesion Expression in Biofilm-Forming *Staphylococcus eepidermidis,*" *Antimicrobial Agents and Chemotherapy*, vol. 44, No. 12, Dec. 2000, pp. 3357-3363.

AATCC Test Method 147-1998, "Antibacterial Activity Assessment of Textile Materials: Parallel Streak Method," 1998, pp. 260-261.

ASTM Designation: E1054-02, "Standard Test Methods for Evaluation of Inactivators of Antimicrobial Agents," Published Aug. 2002, pp. 1-8.

ASTM Designation: E2149-01, "Standard Test Method for Determining the Antimicrobial Activity of Immobilized Antimicrobial Agents Under dynamic Contact Conditions", published Aug. 2001.

ASTM Designation: F1670-03, "Standard Test Method for Resistance of Materials Used in Protective Clothing to Penetration by Synthetic Blood," published Oct. 2003, pp. 1-6.

ASTM Designation: F1671-03, "Standard Test Method for Resistance of Materials Used in Protective Clothing to Penetration by Blood-Borne Pathogens Using Phi-X174 Bacteriophage Penetration as a Test System," published Oct. 2003, pp. 1-10.

ASTM Designation: F1862-00a, "Standard Test Method for Resistance of Medical Face Masks to Penetration by Synthetic Blood (Horizontal Projection of Fixed Volume at a Known Velocity)," published Aug. 2000, pp. 1-9.

ASTM Designation: F2101-01, "Standard Test Method for Evaluating the Bacterial Filtration Efficiency (BFE) of Medical Face Mask Materials, Using a Biological Aerosol of *Staphylococcus aureus*", published Jun. 2001, pp. 1-5.

ASTM Designation: F2299-03, "Standard Test Method for Determining the Initial Efficiency of Materials Used in Medical Face Masks to Penetration by Particulates Using Latex Spheres," published Sep. 2003, pp. 1-8.

INDA Standard Test Method IST 40.2 (01), "Standard Test Method for Electrostatic Decay of Nonwoven Fabrics", 2001, pp. 95-96.

\* cited by examiner

SUBSTRATES PROVIDING MULTIPLE RELEASES OF ACTIVE AGENTS

BACKGROUND

It is common to treat a variety of medical conditions by introducing medical devices into or onto the body. For example, a medical device may be implanted completely or partially into the esophagus, trachea, colon, urinary tract, and vascular system among other areas of a mammalian body. However, medical devices may result in biofilm formation or encrustation while present in the body.

Biofilm formation is a concern with medical devices due to a strong correlation between biofilm formation and infection incidence. To combat this, devices have been impregnated or coated with antimicrobial materials, which provide a slow, steady release of antimicrobials. This is not optimal since slow, steady state elution of antimicrobials can be sub-lethal to pathogens and may contribute to increased antimicrobial resistance. Exposure to sub-lethal antimicrobial concentrations is well-known to potentiate the development of antimicrobial resistance in microbes.

Other devices are available that include coatings of polymeric materials having antimicrobials provided on the surface of medical devices. Some of these medical devices have coatings with multiple polymeric materials and additional time-release coatings to control the release of active agents. However, it would be useful to provide a single type of substrate that may be used with a variety of different devices or materials.

Therefore, creating a way to deliver large initial doses of active agents followed by smaller, steady doses of active agents is desirable. For example, providing multiple doses of an antimicrobial is thought to be more effective in preventing biofilm formation and reducing the likelihood of microbes developing microbial resistance. Additionally, there is a need for technology with such benefits that can be applied to a variety of different medical devices.

SUMMARY

In response to the above described needs, there is provided a substrate for multiple phase delivery of active agents having a first polymer matrix layer with a first active agent disposed therein, a second polymer matrix layer with a second active agent disposed therein, and a coacervate layer disposed between the first polymer matrix layer and the second polymer matrix layer.

In exemplary aspects, the first polymer matrix layer and second polymer matrix layer may contain a polymer selected from polyvinyl chloride, polyurethane, polyethylene, polypropylene, polydiallydimethylammonium chloride, hydrophilic polysaccharides, polylactic acid, polyvinyl alcohol, polyvinylpyrrolidone, acrylates, gums, rubber, silicone, cyanoacrylate, calcium alginate, starch polymers, cellulose, and combinations thereof.

In exemplary aspect, the first polymer matrix and the second polymer matrix are formed from the same polymer. In other aspects, the first polymer matrix has a greater solubility in water or body fluids than the second polymer matrix. In other aspects, the second polymer matrix has a greater solubility in water or body fluids than the first polymer matrix.

In other aspects, the first active agent and the second active agent are selected from antibiotic agents, anti-proliferative agents, anti-inflammatory agents, alcohols, metal salts, innate immunity enhancers, anti-quorumsensing compounds, anti-protozoics, pesticides, preservatives, botanical oils, botanical extracts, and combinations thereof. Specific examples may include quaternary ammonium salts, dodecylguanidine hydrochloride, silver, silver sulfadiazine, chlorohexidine gluconate, polyhexamethylene biguanide, chitosan, triclosan, phospholipids, alpha hydroxyl acids, farnesol, iodine, bromine, hydrogen peroxide, chlorine dioxide, and combinations thereof.

In an exemplary aspect, the first active agent and the second active agent may contain the same active agent. In other aspects, the first active agent and the second active agent are different active agents.

In another exemplary aspect, to easily control the timing of the release of the first and second active agent, a coacervate layer may be disposed between the first polymer matrix layer and the second polymer matrix layer. The coacervate layer may be formed with an anionic surfactant and a cationic surfactant.

The coacervate may contain an anionic surfactant that is selected from alkyl sulfates, alkyl ether sulfates, alkyl ether sulfonates, sulfate esters of an alkylphenoxy polyoxyethylene ethanol, α-olefin sulfonates, β-alkoxy alkyl sulfonates, alkyl lauryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, and/or combinations thereof.

In exemplary aspects, the coacervate may contain a cationic surfactant that is selected from fatty amine salts, alkyl pyridinium salts, quaternary ammonium salts, quaternized amine ethoxylates, alkyl ammonium salts, polymeric ammonium salts, aryl ammonium salts, alkyl aryl ammonium salts, quaternized dimethicones, quaternized silanes, and combinations thereof.

In exemplary aspects, the coacervate can suitably contain anionic surfactants in an amount of from about 50% (by weight of the coacervate layer) to about 99.9% (by weight of the coacervate layer), more typically from about 75% (by weight of the coacervate layer) to about 99.9% (by weight of the coacervate layer), and more preferably from about 90% (by weight of the coacervate layer) to about 99.9% (by weight of the coacervate layer).

In exemplary aspects, the coacervate can suitably contain cationic surfactants in an amount of from about 0.1% (by weight of the coacervate layer) to about 50% (by weight of the coacervate layer), more typically from about 0.1% (by weight of the coacervate layer) to about 25% (by weight of the coacervate layer), and more preferably from about 0.1% (by weight of the coacervate layer) to about 10% (by weight of the coacervate layer).

In an exemplary aspect, the substrate is a wrap accessory adapted to be fitted around an outer surface of a medical device. The medical device may be selected from angiocatheters, PICC lines, central venous catheters, non-tunneled catheters, tunneled catheters, port-a-caths, epideral catheters, tenckhoff catheters, implanted pumps, PEG tubes (feeding), foley catheters, endotracheal tubes, peritoneal dialysis catheters, orthopedic device, implants or devices, needles used for punctures, gowns, face masks, gloves, surgical drapes and incise drapes.

In another exemplary aspect, the substrate is affixed to a wound-facing surface of a bandage, wrap, or wound dressing.

BRIEF DESCRIPTION

DETAILED DESCRIPTION

Generally stated, a polymeric substrate that provides multiple releases of active agents is disclosed. A substrate for multiple releases of active agents is provided having a first polymer matrix layer having at least a first active agent disposed therein, a second polymer matrix layer having at least a second active agent disposed therein, and a coacervate layer disposed between the first polymer matrix layer and the second polymer matrix layer. Selected first and second active agents are included in the first and second polymer matrices such that as the first and second polymer matrices dissolve, the active agents are released.

In an exemplary aspect, multiple phase active agent release is achieved by constructing multiple layers of polymer matrices containing active agents, the polymer matrices formed with polymers having different solubility characteristics.

In an exemplary aspect, the first release of an active agent provides a high initial dose. The outer or first polymer matrix layer may be highly soluble, and thus dissolves quickly, releasing a high dose of the first active agent. In another exemplary aspect, the initial release of the active agent is followed by subsequent antimicrobial releases of either large or small doses, whichever is desired. The inner or second polymer matrix layer is less soluble than the first polymer matrix layer, and thus dissolves slower, releasing the second active agent at a lower dose. Preferably, the subsequent release of active agents is at lower doses in comparison to the initial release and lasts for an extended period of time. The second release of active agent may also be delayed until the coacervate layer is dissolved as well. This is advantageous over technologies that provide only a single slow, steady elution of antimicrobial. The potentially lower quantity of active agent released during a slow, steady elution has a greater likelihood to be sub-lethal to potential pathogens surrounding the substrate. By providing the initial high release of an active agent, these potential pathogens are killed, and a subsequent lower does will suffice to inhibit infection.

Figure 1:
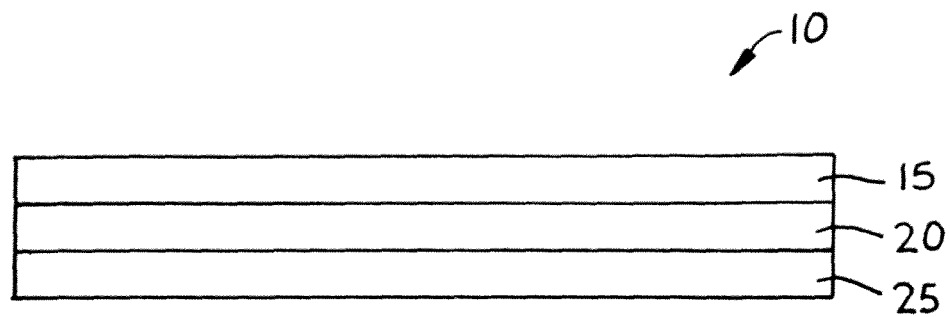
FIG. 1 illustrates a cross-sectional view of an exemplary substrate of the present disclosure.

With reference to FIG. 1, an exemplary substrate 10 for multiple phase delivery of active agents is provided having a first polymer matrix layer 15 having at least a first active agent disposed therein, a second polymer matrix layer 25 having at least a second active agent disposed therein, and a coacervate layer 20 disposed between the first polymer matrix layer 15 and the second polymer matrix layer 25. The coacervate layer 20 serves to adhere the first polymer matrix layer 15 to the second polymer matrix layer 25. Selected first and second active agents are included in the first polymer matrix layer 15 and second polymer matrix layer 25 such that as the first polymer matrix layer 15 and second polymer matrix layer 25 dissolve, the active agents are released. Additional active agents may also be included in the first polymer matrix layer 15 and second polymer matrix layer 25.

The first polymer matrix layer 15 and second polymer matrix layer 25 are formed with materials that are soluble in fluids of mammalian bodies. This allows for release of the active agent disposed therein as each polymer matrix layer dissolves. Exemplary materials include, but are not limited to, polycarboxylic acid polymers and copolymers including polyacrylic acids, acetal polymers and copolymers, acrylate and methacrylate polymers and copolymers, cellulosic polymers and copolymers, including cellulose acetates, cellulose nitrates, cellulose propionates, cellulose acetate butyrates, cellophanes, rayons, rayon triacetates, and cellulose ethers, polyoxymethylene polymers and copolymers, polyimide polymers and copolymers, polysulfone polymers and copolymers, resins including alkyl resins, phenolic resins, urea resins, melamine resins, epoxy resins, alkyl resins and epoxide resins, polycarbonates, polyacrylonitriles, polyvinylpyrrolidones, anhydride polymers and copolymers including maleic anhydride polymers, polymers and copolymers of vinyl monomers including polyvinyl alcohols, polyvinyl halides such as polyvinyl chlorides, ethylene-vinylacetate copolymers, polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers, polyalkyl oxide polymers and copolymers, glycosaminoglycans, polyesters, polyether polymers and copolymers, polyisocyanates, polyolefin polymers and copolymers, including polyalkylenes such as polypropylenes, polyethylenes, polybutylenes, poly-4-methyl-pen-1-enes, ethylene-alpha-olefin copolymers, ethylene-methyl methacrylate copolymers and ethylene-vinyl acetate copolymers, fluorinated polymers and copolymers, including polytetrafluoroethylenes, poly(tetrafluoroethylene-co-hexafluoropropene), modified ethylene-tetrafluoroethylenecopolymers, and polyvinylidene fluorides, silicone polymers and copolymers, polyurethanes, p-xylene polymers, polyiminocarbonates, copoly(ether-esters), polyphosphazines, polyalkylene oxalates, polyoxaamides and polyoxaesters, polyorthoesters; biopolymers, such as polypeptides, proteins, polysaccharides and fatty acids and esters thereof, and combinations thereof.

Preferred materials for use with the substrate of the present disclosure include polyvinyl chloride, polyurethane, polyethylene, polypropylene, polydiallydimethylammonium chloride, hydrophilic polysaccharides, polylactic acid, polyvinyl alcohol, polyvinylpyrrolidone, acrylates, gums, rubber, silicone, cyanoacrylate, calcium alginate, starch polymers, cellulose, and combinations thereof.

The polymer matrix layers can be formed using various known processes. For example, the polymer matrix layers can be formed using solvent-based techniques in which the polymer is first dissolved in a solvent, after which the polymer solution is used to form the matrix portion. In this exemplary aspect, the active agents may be provided within the polymer and solvent mixture in dissolved form or within a particulate suspension and be loaded as the polymer matrix layers are formed.

In an exemplary aspect, disposed between the first polymer matrix layer 15 and second polymer matrix layer 25 is a coacervate layer 20. Use of a coacervate layer 20 allows the timing for the dissolving of the second polymer matrix 25, and thus release of the second active agent, to be controlled. The coacervate layer delays the release of the second active agent as the coacervate layers is dissolved in the body. Only after at least a portion of the coacervate layer dissolves will the second polymer matrix begin to dissolve. Thus, release of the second active agent is controlled to be released at the appropriate time and appropriate duration to inhibit biofilm formation.

In an exemplary aspect, the quantity of active agent delivered at any one time may be controlled by the solubility characteristics of the polymer in each polymer matrix used for the substrate. Thus, as the polymer in the first polymer matrix layer 15 and second polymer matrix layer 25 dissolve within the human body, the active agent is delivered to inhibit infection.

In an exemplary aspect, the first polymer matrix layer 15 of FIG. 1 has a greater solubility in water or body fluids than the second polymer matrix layer 25. Thus, the first polymer matrix layer 15 dissolves quickly and releases the active agent quickly to provide an initial high dose of active agent. Subsequently, the second polymer matrix layer 25 dissolves at a slower pace and releases the active agent at lower dose. In other aspects, the first polymer matrix layer 15 has a lower solubility in water or body fluids than the second polymer matrix layer 25. In this particular aspect, an initial dose of active agent is followed by a subsequent higher dose to ensure that all pathogens remaining by the initial dose are also destroyed.

In another aspect, the concentration of the active agent in each polymer matrix controls the amount of active agent that is released. For example, the first active agent present in the first polymer matrix layer 15 may be in a high concentration to provide an initially high antibiotic, anti-proliferative, or anti-inflammatory effect. The second active agent present in the second polymer matrix layer 25 may be in a lower concentration to provide a subsequent lower dose over a longer time period. The opposite may be true as well, wherein the second active agent present in the second polymer matrix layer 25 may be at a higher concentration and first active agent present in the first polymer matrix layer 25 may be at a lower concentration. In this particular aspect, an initial dose of active agent is followed by a subsequent higher dose to ensure that all pathogens remaining by the initial dose are also destroyed.

In another exemplary aspect, the substrate 10 of the present disclosure includes a first polymer matrix layer 15 and a second polymer matrix layer 25 that are formed from the same polymer.

In exemplary aspects, the active agents disposed within the first polymer matrix layer 15 and second polymer matrix layer 25 are antimicrobials, anti-proliferative agents, anti-inflammatory agents, innate immunity enhancers, permeation enhancers, anti-quorum sensing compounds, anti-protozoics, pesticides, and/or preservatives that could be directed to combat bacteria, viruses, and/or fungi or treat another medical condition. Potential active agents for use include, but are not limited to, antibiotic agents, anti-proliferative agents, anti-inflammatory agents, metal salts, innate immunity enhancers, permeation enhancers, anti-quorum sensing compounds, anti-protozoics, pesticides, preservatives, and combinations thereof. Specific examples include dodecylguanidine hydrochloride, quaternary ammonium salts, silver, silver sulfadiazine, chlorohexidine gluconate, polyhexamethylene biguanide, chitosan, triclosan, phospholipids, alpha hydroxyl acids, farnesol, iodine, bromine, hydrogen peroxide, chlorine dioxide, tea tree oil and rosemary oil, and combinations thereof.

In exemplary aspects, the first active agent and the second active agent may be the same or different active agents. If the active agents are the same, using different polymer matrices may allow for an initial high dose followed by a subsequent lower dose to provide an antibiotic, anti-proliferative, or anti-inflammatory effect. In other aspects, the second active agent is different than the first active agent to target a different purpose than the first active agent. For example, the first active agent could contain a specific antimicrobial agent that targets an individual pathogen, followed by a more general antimicrobial agent that targets numerous threatening pathogens. In another exemplary aspect, the second polymer matrix layer 25 may also contain a second active agent, an anti-inflammatory agent to reduce swelling, in addition to the antibiotic agent in the first polymer matrix layer 15.

As discussed above, the substrate 10 of the present disclosure includes a coacervate layer 20 to provide better timing between release of the first and second active agent. In addition, the coacervate layer 20 may separate different active agents present in the two polymer matrices that may be incompatible. The coacervate layer 20 also adheres the two polymer layers together.

In an exemplary aspect, the coacervate layer 20 may additionally include an active agent therein to provide another release of a particular active agent. In addition, when the coacervate layer is formed with a surfactant, the coacervate layer 20 alone may have some antimicrobial activity. This also may increase the microbial resistance of the substrate.

In an exemplary aspect, the coacervate layer is an anionic component. In another exemplary aspect, the coacervate of the present disclosure contains at least one anionic component and at least one cationic component. In one exemplary aspect, the coacervate layer may contain a copolymer and at least one of the two components selected from a surfactant or a polymer, whereby the copolymer is cationic if the polymer, surfactant, or combination of polymer and surfactant is anionic, or the copolymer is anionic if the polymer surfactant or combination of polymer and surfactant is cationic.

An exemplary coacervate for use with substrate of the present disclosure includes an anionic surfactant and a cationic surfactant. Exemplary anionic surfactants for use in the coacervate layer include alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkylauryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, or combinations thereof. Particular examples of anionic surfactants that may be utilized alone or in combination include, but are not limited to, $C_{8-22}$ alkyl sulfates, $C_{8-22}$ fatty acid salts, $C_{8-22}$ alkyl ether sulfates having one or two moles of ethoxylation, $C_{8-22}$ alkyl ether phosphates having one to three moles of ethoxylation, $C_{8-22}$ alkoyl sarcosinates, $C_{8-22}$ sulfoacetates, $C_{8-22}$ sulfosuccinates, $C_{8-22}$ alkyl diphenyl oxide disulfonates, $C_{8-22}$ alkyl carbonates, $C_{8-22}$ alpha-olefin sulfonates, methyl ester sulfonates, and blends thereof. The $C_{8-22}$ alkyl group may be a straight chain (e.g., lauryl) or branched (e.g., 2-ethylhexyl). The cation of the anionic surfactant may be an alkali metal (e.g., sodium or potassium), ammonium, $C_{1-4}$ alkylammonium (e.g., mono-, di-, tri-), or $C_{1-3}$ alkanolammonium (e.g., mono-, di-, tri). More specifically, such anionic surfactants may include, but are not limited to, lauryl sulfates, octyl sulfates, 2-ethylhexyl sulfates, potassium laureth phosphate, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, cetyl sulfates, and similar surfactants.

In a particular aspect, MIPA-laureth sulfate in the presence of the glycol carrier (Marlinat 242-90M commercially available from Sasol North America Inc. of Houston, Tex.) is used as the anionic surfactant in the coacervate. In another particular aspect, TIPA-laureth sulfate (Marlinat 242-90T commercially available from Sasol North America Inc. of Houston, Tex.) in the presence of the glycol carrier is used as the anionic surfactant in the coacervate layer.

The coacervate layer may include anionic surfactants. Desirably, the coacervate layer can suitably contain anionic surfactants in an amount of from about 50% (by weight of the coacervate layer) to about 99.9% (by weight of the coacervate layer), more typically from about 75% (by weight of the coacervate layer) to about 99.9% (by weight of the coacervate layer), and more preferably from about 90% (by weight of the coacervate layer) to about 99.9% (by weight of the coacervate layer).

Exemplary cationic surfactants for use in coacervate include, but are not limited to, fatty amine salts, alkyl pyridinium salts, quaternary ammonium salts, quaternized amine ethoxylates, alkyl ammonium salts, polymeric ammonium salts, aryl ammonium salts, alkyl aryl ammonium salts, quaternized dimethicones, quaternized silanes, and combinations thereof. Specific examples of cationic surfactants for use in the modified surfactant composition include, but are not limited to, polyquaternium-7, polyquaternium-10, behentrimonium chloride, stearalkonium chloride, distearalkonium chloride, chlorhexidine digluconate, polyhexamethylene biguanide (PHMB), polyaminopropyl biguanide, cetylpyridinium chloride, benzammonium chloride, benzalkonium chloride, behentrimonium methosulfate, cetrimonium chloride, cocamidopropyl pg-dimonium chloride, guar hydroxypropyltrimonium chloride, isostearamidopropyl morpholine lactate, quaternium-80, polyquaternium-33, polyquaternium-60, polyquaternium-79, quaternium-18 hectorite, quaternium-79 hydrolyzed silk, quaternium-79 hydrolyzed soy protein, rapeseed amidopropyl ethyldimonium ethosulfate, silicone quaternium-7, stearalkonium chloride, palmitamidopropyltrimonium chloride, butylglucosides, hydroxypropyltrimonium chloride, laurdimoniumhydroxypropyl decylglucosides chloride, and the like.

In a particular aspect, Quaternarium-80 (Abil QUAT-3473 commercially available from Evonik Industries of Hopewell, Va.) is used as the cationic surfactant in the coacervate layer.

In exemplary aspects, the coacervate layer can suitably contain cationic surfactants in an amount of from about 0.1% (by weight of the composition) to about 50% (by weight of the composition), more typically from about 0.1% (by weight of the composition) to about 25% (by weight of the composition), and more preferably from about 0.1% (by weight of the composition) to about 10% (by weight of the composition).

The substrate of the present disclosure may be manufactured and delivered in the form of an accessory wrap or covering that could be placed onto a wide array of medical devices. Examples of devices where this substrate could be employed include, but is not limited to, angiocatheters, PICC lines, central venous catheters, non-tunneled catheters, tunneled catheters, port-a-caths, epideral catheters, tenckhoff catheters, implanted pumps, PEG tubes (feeding), foley catheters, endotracheal tubes, peritoneal dialysis catheters, orthopedic device, implants or devices, needles used for punctures, gowns, face masks, surgical drapes, gloves, and incise drapes.

Each of these medical devices has different shapes and sizes that may present a challenge in placing a protective covering or wrap. As discussed above, the substrate of the present disclosure may be manufactured and delivered in the form of an accessory wrap or covering. The wrap or covering is versatile and flexible enough to use on different devices. Thus, the wrap can be formed around different types of devices and manipulated into small areas present on the surface of the medical device. Thus, the wrap may be purchased separately and placed onto different medical devices or be used for specific infection controls.

The covering or wrap may be attached to the medical device by any known process by one skilled in the art. For example, adhesives, such as acrylic, may be applied to the surface of the substrate 10 that will be attached to the medical device.

Figure 2:
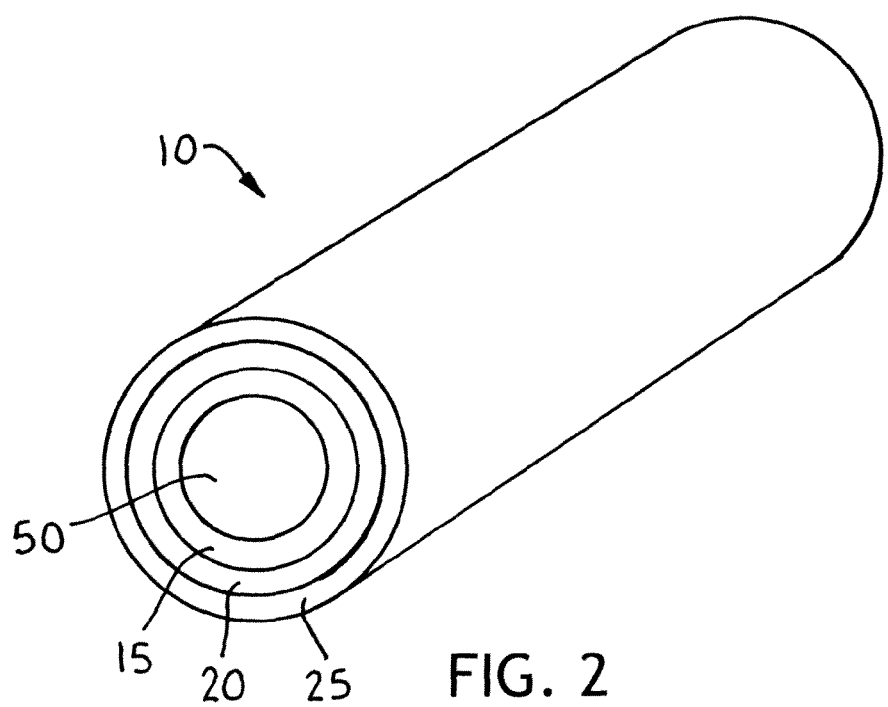
FIG. 2 illustrates a cross-sectional view of the exemplary substrate of the present disclosure on an exemplary medical device.

An exemplary medical device having the substrate of the present disclosure placed thereon is illustrated in FIG. 2. In this aspect, a tubular portion of a medical device 50 is covered with a substrate 10 includes a first polymer matrix layer 15, within which is disposed one or more active agents. A coacervate layer 20 is disposed over the first polymer matrix layer 15. Disposed on the coacervate layer is a second polymer matrix layer 25, within which is disposed one or more active agents. The substrate 10 may or may not be permanently in place for the entire duration of device usage. Preferably, the coating, wrap, or covering would dissolve following complete release of the active agent.

Figure 3:
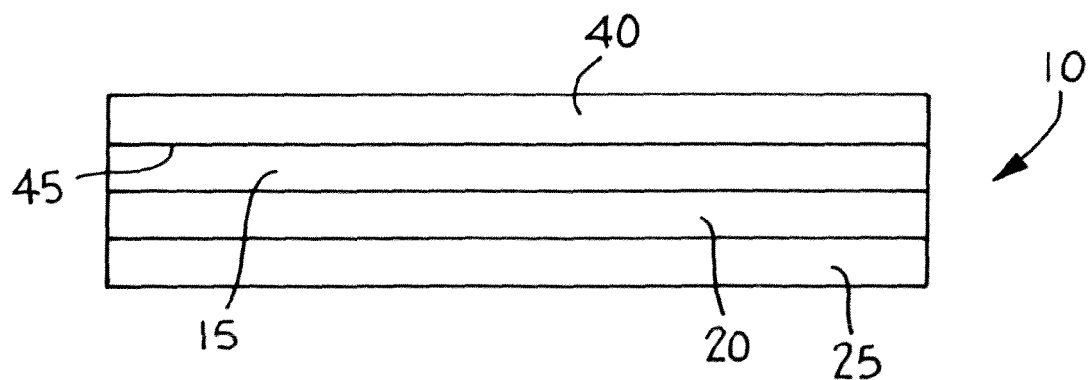
FIG. 3 illustrates another cross-sectional view of the exemplary substrate of the present disclosure present on an exemplary substrate.

In another exemplary aspect, as illustrated in FIG. 3, the substrate 10 of the present disclosure may also be incorporated onto a bandage, wrap or dressing 40. In this aspect, an absorbent wound dressing 40 having the substrate 10 of the present disclosure having a mechanism for release of multiple active agents is affixed onto the wound-facing side 45 of the bandage, wrap or dressing 40. The substrate would provide a therapeutic effect to the wound as the polymer matrix layers dissolve.

A preferred absorbent layer is a foam, woven or nonwoven material including, but not limited to, rayon, polyester, polyurethane, polyolefin, cellulose, cellulose derivatives, cotton, orlon, nylon, or hydrogel polymeric materials. An alternative absorbent layer includes a composite material comprising a nonwoven polymeric matrix and a highly hydrophilic fluid absorbing material. A particularly preferred composite material is a nonwoven matrix combined with a highly hydrophilic fluid absorbing material such as a polymeric absorbent fiber or particle selected from the group consisting of modified starches and high molecular weight acrylic polymers containing hydrophilic groups such as acrylonitrile fibers treated with alkali metal hydroxides. Suitable absorbent materials will preferably absorb at least about 25% by weight of fluid or exudate, and more preferably greater than about 100% by weight.

A variety of means are suitable for attaching or fixing the substrate 10 to the absorbent layer 40 such as stitching, needle-tacking, ultrasonic welding or bonding with a suitable adhesive.

The substrate 10 may or may not be permanently in place for the entire duration of device or dressing usage. Preferably, substrate 10 would completely dissolve following complete release of the active agent.

In addition to medical devices, the substrate may also be used for other applications. For example, the substrate could also be utilized to prevent pathogen formation on such surfaces such as air vents, water lines, air and water filters, and hard surfaces (e.g., showers, countertops).

Additionally, the substrate may be used to deliver other actives as well. For example, the polymer matrices may further have additional agents that impart a beneficial effect on skin or hair and/or further act to improve the aesthetic feel of the substrate described herein. Examples of suitable skin benefit agents include emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, and the like.

Thus, in one aspect, the compositions may further optionally include one or more emollients, which typically act to soften, soothe, and otherwise lubricate and/or moisturize the skin. Suitable emollients that can be incorporated into the compositions include oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof.

Suitable esters as emollients could include, but not be limited to, cetyl palmitate, stearyl palmitate, cetyl stearate, isopropyl laurate, isopropyl myristate, isopropyl palmitate, and combinations thereof. The fatty alcohols as emollients could include but not be limited to octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

Sterol and sterol derivatives which are suitable for use in the compositions of the present disclosure include, but are not limited to, cholesterol, sitosterol, stigmasterol, ergosterol, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrolanosterol, dihydrolanosteryl octyidecanoate, ergocalciferol, tall oil sterol, soy sterol acetate, lanasterol, soy sterol, avocado sterols, fatty alcohols, and combinations thereof.

The compositions of the disclosure can also include natural fats and oils. As used herein, the term "natural fat or oil" is intended to include fats, oils, essential oils, essential fatty acids, non-essential fatty acids, phospholipids, and combinations thereof. These natural fats and oils can provide a source of essential and non-essential fatty acids to those found in the skin's natural barrier. Suitable natural fats or oils can include citrus oil, olive oil, avocado oil, apricot oil, babassu oil, borage oil, camellia oil, canola oil, castor oil, coconut oil, corn oil, cottonseed oil, emu oil, evening primrose oil, hydrogenated cottonseed oil, hydrogenated palm kernel oil, jojoba oil, maleated soybean oil, meadowfoam oil, palm kernel oil, peanut oil, rapeseed oil, grapeseed oil, safflower oil, sphingolipids, sweet almond oil, tall oil, lauric acid, palmitic acid, stearic acid, linoleic acid, stearyl alcohol, lauryl alcohol, myristyl alcohol, behenyl alcohol, rose hip oil, calendula oil, chamomile oil, eucalyptus oil, juniper oil, sandlewood oil, tea tree oil, sunflower oil, soybean oil, and combinations thereof.

The compositions of the disclosure may optionally further comprise humectants. Examples of suitable humectants include glycerin, glycerin derivatives, sodium hyaluronate, betaine, amino acids, glycosaminoglycans, honey, sorbitol, glycols, polyols, sugars, hydrogenated starch hydrolysates, salts of PCA, lactic acid, lactates, and urea. A particularly preferred humectant is glycerin.

The compositions of the disclosure may optionally further contain moisturizers. Examples of suitable moisturizers include light hydrocarbon oil (e.g., mineral oil, isododecane, petrolatum), vegetable or natural oil (e.g., sunflower oil, olive oil, sweet almond oil, grapeseed oil, corn oil, safflower oil, shea butter, coconut oil, canola oil, castor oil, jojoba oil), hydrogenated vegetable oil (e.g., hydrogenated castor wax, hydrogenated apricot kernel oil, hydrogenated canola oil, hydrogenated jojoba oil, hydrogenated olive oil, hydrogenated sesame seed oil), fatty ester (e.g., octyldodecyl neopentanoate, stearyl stearate, isopropyl myristate, isopropyl palmitate, stearyl behenate, $C_{12}$-$C_{15}$ alkyl benzoate, butyl isostearate, cetyl caprate, cetyl caprylate, ethyl apricot kernelate, ethyl avocadate, ethylhexyl caprate/caprylate, ethylhexyl cocoate, ethylhexyl isopalmitate, isocetyl myristate, isopropyl jojobate, myristyl laurate), fatty acid (e.g., palmitic acid, stearic acid, myristic acid, oleic acid, linoleic acid, behenic acid), fatty alcohol (e.g., lauryl alcohol, cetyl alcohol, stearyl alcohol, behenyl alcohol), or combinations thereof. In one aspect, the composition may contain a fatty ester as a carrier. One example of a fatty ester is isopropyl myristate, which is available under the name TEGOSOFT M (commercially available from Evonik Industries of Hopewell, Va.).

The compositions of the disclosure may optionally further contain film formers. Examples of suitable film formers include petrolatum, emollient esters, lanolin derivatives (e.g., acetylated lanolins), superfatted oils, cyclomethicone, cyclopentasiloxane, dimethicone, natural and synthetic oils, fatty acids, fatty alcohols, waxes, synthetic and biological polymers, proteins, quaternary ammonium materials, starches, gums, cellulosics, polysaccharides, albumen, acrylates derivatives, IPDI derivatives, and the like.

The compositions of the disclosure may optionally further contain slip modifiers. Examples of suitable slip modifiers include bismuth oxychloride, iron oxide, mica, surface treated mica, ZnO, $ZrO_2$, silica, silica silyate, colloidal silica, attapulgite, sepiolite, starches (e.g., corn, tapioca, rice), cellulosics, nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, bismuth oxychloride, iron oxide, aluminum oxide, silicone resin, barium sulfate, calcium carbonate, cellulose acetate, polymethyl methacrylate, polymethylsilsequioxane, talc, tetrafluoroethylene, silk powder, boron nitride, lauroyl lysine, synthetic oils, natural oils, esters, silicones, glycols, and the like.

The compositions of the disclosure may optionally further contain surface modifiers. Examples of suitable surface modifiers include silicones, quaternium materials, powders, salts, peptides, polymers, clays, and glyceryl esters.

The compositions of the disclosure may optionally further contain skin protectants. Examples of suitable skin protectants include ingredients referenced in SP monograph (21 CFR §347). Suitable skin protectants and amounts include those set forth in SP monograph, Subpart B—Active Ingredients §347.10: (a) Allantoin, 0.5% to 2%, (b) Aluminum hydroxide gel, 0.15% to 5%, (c) Calamine, 1 to 25%, (d) Cocoa butter, 50% to 100%, (e) Cod liver oil, 5% to 13.56%, in accordance with §347.20(a)(1) or (a)(2), provided the product is labeled so that the quantity used in a 24-hour period does not exceed 10,000 U.S.P. Units vitamin A and 400 U.S.P. Units cholecalciferol, (f) Colloidal oatmeal, 0.007% minimum; 0.003% minimum in combination with mineral oil in accordance with §347.20(a)(4), (g) Dimethicone, 1% to 30%, (h) Glycerin, 20% to 45%, (i) Hard fat, 50% to 100%, (j) Kaolin, 4% to 20%, (k) Lanolin, 12.5% to 50%, (l) Mineral oil, 50% to 100%; 30% to 35% in combination with colloidal oatmeal in accordance with §347.20(a)(4), (m) Petrolatum, 30% to 100%, (o) Sodium bicarbonate, (q) Topical starch, 10% to 98%, (r) White petrolatum, 30% to 100%, (s) Zinc acetate, 0.1% to 2%, (t) Zinc carbonate, 0.2% to 2%, (u) Zinc oxide, 1% to 25%.

The compositions of the disclosure may optionally further contain sunscreens. Examples of suitable sunscreens include aminobenzoic acid, avobenzone, cinoxate, dioxybenzone, homosalate, menthyl anthranilate, octocrylene, octinoxate, octisalate, oxybenzone, padimate O, phenylbenzimidazole sulfonic acid, sulisobenzone, titanium dioxide, trolamine salicylate, zinc oxide, and combinations thereof. Other suitable sunscreens and amounts include those approved by the FDA, as described in the Final Over-the-Counter Drug Products Monograph on Sunscreens (Federal Register, 1999:64: 27666-27693), herein incorporated by reference, as well as European Union approved sunscreens and amounts.

The compositions of the disclosure may optionally further contain additional surfactants. Examples of suitable surfactants include, for example, amphoteric surfactants, zwitterionic surfactants, non-ionic surfactants, and combinations thereof. Specific examples of suitable surfactants are known in the art and include those suitable for incorporation into personal care compositions and wipes.

The compositions of the disclosure may optionally further contain additional emulsifiers. Examples of suitable emulsifiers include nonionics such as polysorbate 20, polysorbate 80, anionics such as DEA phosphate, cationics such as behentrimonium methosulfate, and the like.

The composition of the present disclosure may additionally include adjunct components conventionally found in pharmaceutical compositions in their art-established fashion and at their art-established levels. For example, the compositions may contain additional compatible pharmaceutically active materials for combination therapy, such as astringents, keratolytic actives, local anaesthetics, anti-stinging agents, anti-reddening agents, skin soothing agents, and combinations thereof. Other suitable additives that may be included in the compositions of the present disclosure include colorants, deodorants, fragrances, perfumes, emulsifiers, anti-foaming agents, lubricants, natural moisturizing agents, skin conditioning agents, skin protectants and other skin benefit agents (e.g., extracts such as aloe vera and anti-aging agents such as peptides), solvents, solubilizing agents, suspending agents, wetting agents, humectants, preservatives, propellants, dyes and/or pigments, and combinations thereof.

As various changes could be made in the above substrates/articles without departing from the scope of the disclosure, it is intended that all matter contained in the above description shall be interpreted as illustrative and not in a limiting sense.

EXAMPLE

The following non-limiting example is provided to further illustrate the present disclosure.

To illustrate the ability of the substrate having multiple polymer matrix layers to release active agents at multiple intervals, flourescein and rhodamine were incorporated into different polymers. These two molecules are fluorophores used as surrogate active agents that contain functional groups and have the ability to absorb energy of a specific wavelength and re-emit energy at a different wavelength. Using a fluorescent spectrophotometer, samples to be analyzed are irradiated by excitation light which causes the sample to emit fluorescence light at characteristic wavelengths. The fluorescence light is measured by a suitable detector to derive information about the sample, in particular the composition of the sample and the quantities of the individual components present in the sample are detected. Rhodamine is detected using an excitation wavelength of 527 nm and emission wavelength of 547 nm. Fluorescein is detected using an excitation wavelength of 495 nm and emission wavelength of 520 nm.

First, a first polymer matrix was prepared by dissolving a polyvinyl alcohol polymer, Celvel, (commercially available from Celanese Corporation of Dallas, Tex.), in 1× phosphate-buffered saline at 0.025 g/ml using heat. Fluorescein was incorporated into this polymer as a surrogate active component by adding 10 mg/ml fluorescein sodium salt (Sigma-Aldrich F6377 commercially available from Sigma-Aldrich of St Louis, Mo.) to prepare a 0.1 mg flourescein/gram polymer mixture. This solution was then put into a glass Petri dish and wrapped in tinfoil to protect the fluorescein from light exposure and allowed to dry in a 50° C. incubator for about 3 days until no liquid was visible.

Subsequently, a second polymer matrix was formed with a 40:60 ratio by weight mixture of polyurethane, Desmopan (commercially available from Bayer Material Science LLC of Pittsburgh, Pa.), and polyvinyl alcohol, Elvanol (commercially available from DuPont Company of Wilmington, Del.), by dissolving the mixture in 1× phosphate-buffered saline at 0.025 g/ml. The second polymer matrix has slower dissolution characteristics than the first polymer matrix formed. Rhodamine was incorporated into this polymer as a surrogate active by adding 10 mg/ml rhodamine 6G (Sigma-Aldrich 252433 commercially available from Sigma-Aldrich of St Louis, Mo.) was added to make a 0.1 mg rhodamine/gram polymer mixture. Approximately, 850 µl of this solution was added to each well of a 24 well plate and was wrapped in tinfoil to protect the rhodamine from light exposure and allowed to dry in a 50° C. incubator about 3 days until no liquid was visible.

A coacervate was prepared by combining 6.0% by weight of a cationic surfactant, quaternium-80 (commercially available from Evonik Industries of Hopewell, Va.), and 94.0% by weight of an anionic surfactant, MIPA-laureth sulfate (commercially available from Sasol North America, Inc. of Houston, Tex.), and mixing together until homogeneous.

When the polymers matrices were dry, the first polymer matrix, second polymer matrix and the coacervate were formed into layers. The prepared second polymer matrix layer was then wrapped inside a 2.0 g of the prepared coacervate layer. The resulting two-layer system was then wrapped in a 0.1 g piece of the dried first polymer matrix layer to form a ball of an exemplary substrate of the present disclosure. Three samples of the substrate were prepared.

The three samples were then placed into separate vessels containing 5 ml of 1× phosphate-buffered saline at room temperature. Three aliquots were taken from each vessel at time intervals of 0, 1, 15, 60, 120 and 240 minutes. Each aliquot was then tested using the spectrophotometer to illustrate the amount of each active agent released. The average values for fluorescence release of each active agent were determined for each time interval. The highest level of release of fluorescence for each surrogate active agent is considered to be the maximum concentration level of release.

Figure 4:
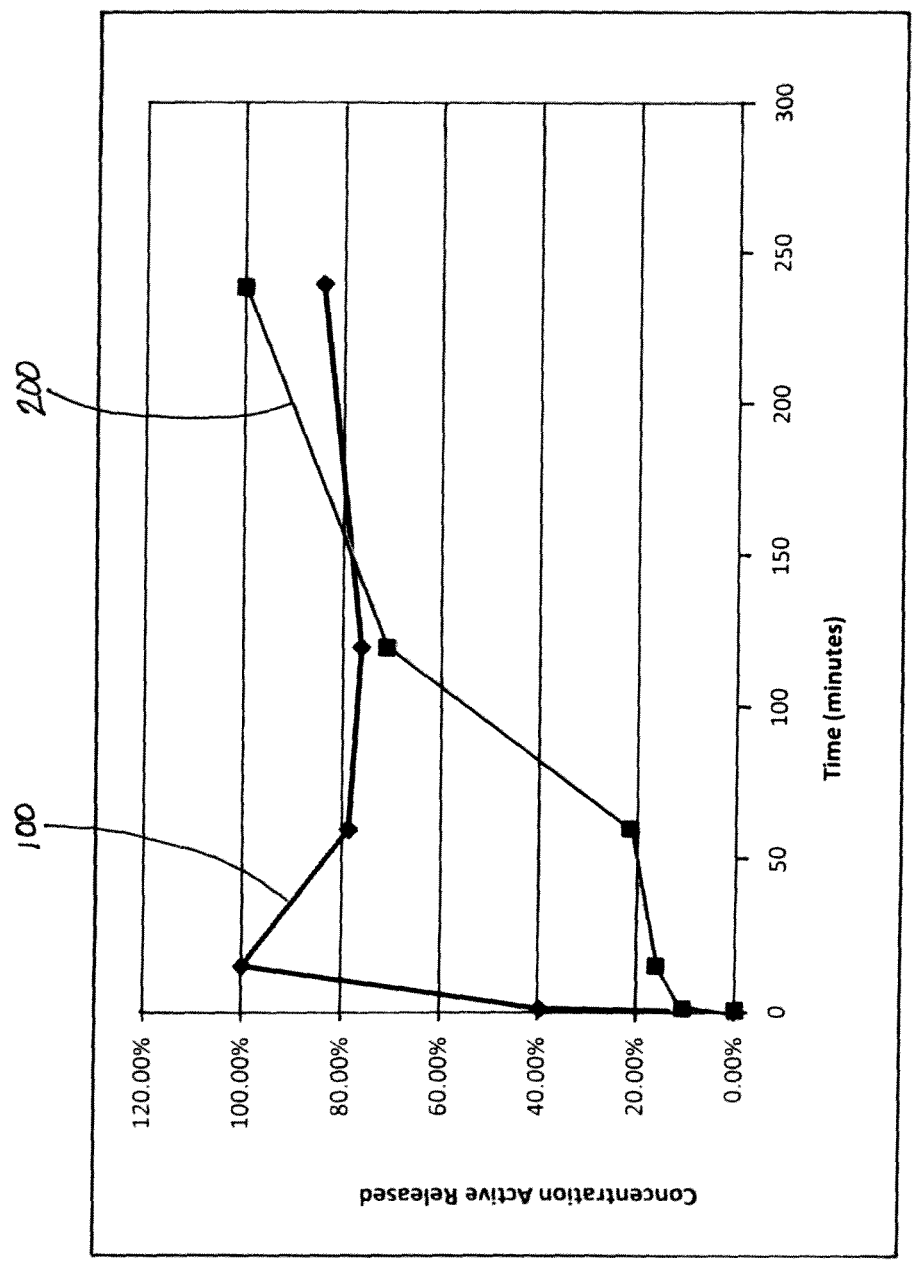
FIG. 4 illustrates the release of surrogate active agents from an exemplary substrate of the present disclosure.

As illustrated in FIG. 4, the substrate of the present disclosure allows active agents to be released at different time intervals. The release of the first active agent, fluorescein, is illustrated by curve 100. As illustrated, the first active agent, flourescein, very quickly reached 100% concentration level within 15 minutes after placement into the saline solution as the first polymer layer dissolved. The flourescein concentration then began to level off. Subsequently, the second active agent, rhodamine, initially only released at low concentrations and did not reach 100% concentration level until 240 minutes after placement into the saline solution. The release of the second active agent, rhoadmine, is illustrated by curve 200. Use of a second polymer matrix that has slower dissolution characteristics allows for a slower release of the second active agent. Additionally, as illustrated by FIG. 4, use of a coacervate layer helped to delay the initial release of the second active agent.

Having described the disclosure in detail, it will be apparent that modifications and variations are possible without departing from the scope of the disclosure defined in the appended claims.

The invention claimed is:

1. A substrate for multiple releases of active agents comprising:
   a coacervate layer comprising an anionic surfactant present in an amount of from about 50% (by weight of the coacervate layer) to about 99.9% (by weight of the coacervate layer), and a cationic surfactant present in an amount of from about 0.1% (by weight of the coacervate layer) to about 50% (by weight of the coacervate layer);
   a first polymer matrix layer having at least a first active agent disposed therein, wherein the first active agent is released when the first polymer matrix dissolves;
   a second polymer matrix layer having at least a second active agent disposed therein, wherein the second active agent is released when the second polymer matrix dissolves; and
   wherein the coacervate layer is disposed between and adheres together the first polymer matrix layer and the second polymer matrix layer;
   wherein the first polymer matrix is configured to dissolve prior to the dissolution of the coacervate layer, and the coacervate layer is configured to dissolve prior to the dissolution of the second polymer matrix; and
   wherein the first active agent and the second active agent are different active agents.

2. The substrate of claim 1 wherein the first polymer matrix layer and second polymer matrix layer comprises a material selected from polyvinyl chloride, polyurethane, polyethylene, polypropylene, polydiallydimethylammonium chloride, rubber, silicone, cyanoacrylate, calcium alginate, starch polymers, cellulose, hydrophilic polysaccharides, polylactic acid, polyvinyl alcohol, polyvinylpyrrolidone, acrylates, gums, and combinations thereof.

3. The substrate of claim 1 wherein the first polymer matrix and the second polymer matrix are formed from the same polymer.

4. The substrate of claim 1 wherein the first polymer matrix has a greater solubility in fluid of a mammalian body than the second polymer matrix.

5. The substrate of claim 1 wherein the first polymer matrix has a lower solubility in fluid of a mammalian body than the second polymer matrix.

6. The substrate of claim 1 wherein the first active agent and the second active agent are selected from antibiotic agents, anti-proliferative agents, anti-inflammatory agents, metal salts, innate immunity enhancers, permeation enhancers, anti-quorum sensing compounds, anti-protozoics, pesticides, preservatives, alcohols, botanical oils, botanical extracts, and combinations thereof.

7. The substrate of claim 1 wherein the anionic surfactant is selected from alkyl sulfates, alkyl ether sulfates, alkyl ether sulfonates, sulfate esters of an alkylphenoxy polyoxyethylene ethanol, α-olefin sulfonates, β-alkoxy alkane sulfonates, alkylauryl sulfonates, alkyl monoglyceride sulfates, alkyl monoglyceride sulfonates, alkyl carbonates, alkyl ether carboxylates, alkyl phosphates, alkyl ether phosphates, sulfosuccinates, sarcosinates, octoxynol or nonoxynol phosphates, taurates, fatty acid amide polyoxyethylene sulfates, isethionates, and/or combinations thereof.

8. The substrate of claim 1 wherein the cationic surfactant is selected from fatty amine salts, alkyl pyridinium salts, quaternary ammonium salts, quaternized amine ethoxylates, alkyl ammonium salts, polymeric ammonium salts, aryl ammonium salts, alkyl aryl ammonium salts, quaternized dimethicones, quaternized silanes and combinations thereof.

9. The substrate of claim 1 wherein the anionic surfactant is present in present in an amount from about 75% (by weight of the coacervate layer) to about 99.9% (by weight of the coacervate layer).

10. The substrate of claim 1 wherein the cationic surfactant is present in an amount from about 0.1% (by weight of the coacervate layer) to about 25% (by weight of the coacervate layer).

11. The substrate of claim 1 wherein the coacervate layer has at least one active agent disposed therein.

12. The substrate of claim 1 wherein the substrate is an accessory wrap adapted to be placed around the outer surface of a medical device.

13. The substrate of claim 12 wherein the medical device is selected from angiocatheters, PICC lines, central venous catheters, non-tunneled catheters, tunneled catheters, port-a-caths, epideral catheters, tenckhoff catheters, implanted pumps, PEG tubes (feeding), foley catheters, endotracheal tubes, peritoneal dialysis catheters, orthopedic device, implants or devices, needles used for punctures, gloves, face masks, gowns, surgical drapes and incise drapes.

14. The substrate of claim 1 wherein the substrate is affixed to a wound-facing surface of a bandage, wrap, or wound dressing.

15. The substrate of claim 1 wherein the substrate is affixed to air vents, water lines, air and water filters, or hard surfaces.

16. The substrate of claim 1 wherein the active agent is selected from astringents, keratolytic actives, local anaesthetics, anti-stinging agents, anti-reddening agents, skin soothing agents, colorants, deodorants, fragrances, perfumes, emulsifiers, anti-foaming agents, lubricants, natural moisturizing agents, skin conditioning agents, skin protectants, skin benefit agents solvents, solubilizing agents, suspending agents, wetting agents, humectants, preservatives, propellants, dyes and/or pigments, and combinations thereof.

* * * * *